United States Patent [19]

Talley

[11] Patent Number: 4,584,417

[45] Date of Patent: Apr. 22, 1986

[54] METHOD FOR PREPARING P-ALKYLPHENOLS FROM P-HYDROXYALKYLPHENOLS

[75] Inventor: John J. Talley, Clifton Park, N.Y.

[73] Assignee: General Electric Company, Schenectady, N.Y.

[21] Appl. No.: 577,098

[22] Filed: Feb. 6, 1984

[51] Int. Cl.$^4$ ............................................. C07C 37/00
[52] U.S. Cl. .................................... 568/799; 568/780; 568/782; 568/802
[58] Field of Search ............... 568/802, 799, 800, 741, 568/772, 782, 771, 740

[56] References Cited

U.S. PATENT DOCUMENTS 2,625,570  1/1953  Pines et al. ........................ 568/716

FOREIGN PATENT DOCUMENTS 1270731  7/1961  France ................................ 568/799
6515080  5/1968  Netherlands ....................... 568/799

OTHER PUBLICATIONS

Mitsui et al, "Chemical Abstracts", vol. 57, p. 3341 (1962).

Primary Examiner—Werren B. Lone
Attorney, Agent, or Firm—William H. Pittman; James C. Davis, Jr.; James Magee, Jr.

[57] ABSTRACT p-Alkylphenols such as p-cresol are prepared by the reaction of p-hydroxyalkylphenols with water and oxygen in the presence of at least one oxide of a Group II metal having an atomic weight less than 70, preferably zinc oxide. At least part of the p-hydroxyalkylphenol contains a p-hydroxymethyl group, and it is preferably entirely p-hydroxybenzyl alcohol. The reaction temperature is about 350°–550° C.

7 Claims, 4 Drawing Figures

FIG. I
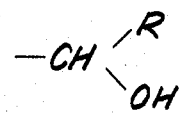
FIG. II
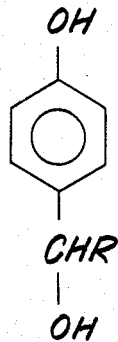
FIG. III
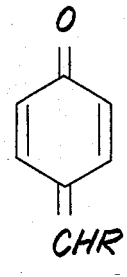
FIG. IV
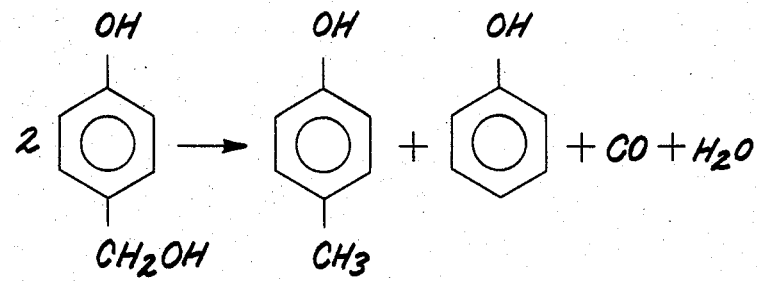

METHOD FOR PREPARING P-ALKYLPHENOLS FROM P-HYDROXYALKYLPHENOLS

This invention relates to the preparation of p-alkylphenols, and more particularly to their preparation by a novel method for the catalytic reduction of p-hydroxyalkylphenols.

p-Alkylphenols such as p-cresol are known to be useful chemical materials. Their uses are illustrated by those of p-cresol (p-methylphenol), which is an intermediate for the preparation of other chemicals and which can also be used as a disinfectant and antioxidant. In view of these uses, it is of interest to develop new methods for the preparation of p-cresol and other p-alkylphenols.

A principal object of the present invention, therefore, is to provide a novel method for the preparation of p-alkylphenols.

A further object is to provide a catalytic method for such preparation, said method employing relatively inexpensive starting materials.

Other objects will in part be obvious and will in part appear hereinafter.

In its broadest aspect, the present invention is a method for preparing a p-alkylphenol in which the para-substituent has the formula $CH_2R$, wherein R is hydrogen, an alkyl radical containing about 1–4 carbon atoms or phenyl, which comprises contacting at least one p-hydroxyalkylphenol in which the para-substituent has the formula in FIG. I in the drawings, at least part of said p-hydroxyalkylphenol being one in which R is hydrogen, with water and oxygen at a temperature in the range of about 350°–550° C., in the presence of at least one oxide of a Group II metal having an atomic weight less than 70.

The drawing includes three chemical formulas and a chemical equation.

FIG. I depicts the substituent formula to which reference is made hereinabove, and FIG. II depicts the corresponding p-hydroxyalkylphenol.

FIG. III depicts a quinone methide and the equation of FIG. IV represents a reaction sequence pertinent to the invention, both more fully identified hereinafter.

As will be apparent, the principal reactant in the method of this invention is at least one p-hydroxyalkylphenol having the formula in FIG. II. For reasons explained hereinafter, at least part of said p-hydroxyalkylphenol is p-hydroxybenzyl alcohol. It is most often entirely p-hydroxybenzyl alcohol since p-cresol, the product obtained therefrom, is the most widely used p-alkylphenol. However, it is within the scope of the invention to employ p-hydroxyalkylphenol mixtures containing up to about 50 mole percent of compounds in which the R value is phenyl or an alkyl radical containing about 1–4 carbon atoms, such as methyl, ethyl, 1-propyl, 2-propyl, 1-butyl or t-butyl.

In addition to the radical of FIG. I, the p-hydroxyalkylphenol may contain other substituents which are inert under the conditions of the method of this invention, such as halide (especially chloride or bromide), amino or sulfide. It may also contain alkyl substituents, usually those having from 1 to about 4 carbon atoms. Depending on the severity of the reaction conditions, alkyl substituents in positions ortho to the phenolic hydroxy group may be removed by dealkylation under the conditions of the method of this invention. For example, 4-hydroxymethyl-2,6-dimethylphenol may also be converted to p-cresol. Such dealkylation reactions are disclosed and claimed in, commonly assigned U.S. Pat. No. 4,533,767 and U.S. Pat. No. 4,533,768. Nevertheless, the presence of such substituents in the starting material is still within the scope of the invention.

The catalyst species useful in the method of this invention are oxides of Group II metals having an atomic weight less than 70. These include beryllium, magnesium, calcium and zinc. The oxides of these metals are represented by the formula MO, wherein M is the metal. Because of their low cost and availability, magnesium, calcium and zinc are preferred, with zinc being particularly preferred because of its effectiveness in the method of the invention. It is also within the scope of the invention to use mixtures of said metal oxides.

The method of this invention also requires water and oxygen as reagents. Pure oxygen may be used, but the use of gas mixtures containing oxygen is preferred, the preferred gas mixture being air. Under the prevailing temperature conditions, the water is present as steam.

The method involves contacting the mixture of p-hydroxyalkylphenol, water and oxygen with the Group II metal oxide catalyst at a temperature in the range of about 350°–550° C. When the reaction is effected at atmospheric pressure, temperatures of 450°–500° C. are preferred. Higher pressures, usually up to about 100 psig., may also be employed whereupon the use of lower temperatures, ordinarily about 400°–450° but on occasion as low as 350° C., is often possible.

The proportions of reagents employed are not critical. In order to maximize yields, the use of an excess of water and oxygen is normal. It is most often convenient to pass the reactant mixture over the catalyst at a relatively constant velocity, and this velocity may be chosen in a manner understood by those in the art to maximize p-alkylphenol yield, taking into consideration the amount of catalyst used. When the effectiveness of the catalyst decreases, it may be easily regenerated by merely contacting with oxygen, either pure or in the form of a mixture such as air, at a temperature similar to that utilized for preparation of the p-alkylphenol.

It may sometimes be desirable to employ a diluent for the p-hydroxyalkylphenol, particularly when it is a solid material at the temperatures at which it is fed into the system. The solvent employed should be one which does not undergo substantial decomposition under the reaction conditions, although a small amount of decomposition will frequently not be deleterious. Illustrative solvents are aliphatic hydrocarbons such as petroleum naphtha having an appropriate boiling range, aromatic hydrocarbons such as benzene and toluene, and ethers such as tetrahydrofuran.

While the present invention is not dependent on any reaction theory or mechanism, it is believed that one step is the dehydration of the p-hydroxyalkylphenol to a quinone methide having the formula in FIG. III. At substantially the same time, a portion of the p-hydroxyalkylphenol reactant in which R is hydrogen eliminates formaldehyde to form the corresponding phenol, and the formaldehyde decomposes to carbon monoxide and hydrogen. The hydrogen then reduces the quinone methide to the p-alkylphenol. When p-hydroxymethylphenol is the sole p-hydroxyalkylphenol employed, the overall reaction sequence may be represented by the equation in FIG. IV.

Based on the above-described mechanism, the necessity for R to be hydrogen in at least a portion of the p-hydroxyalkylphenol will be understood: a formaldehyde-generating species is essential since formaldehyde is the source of the hydrogen which reduces the quinone methide. For stoichiometry reasons which will be evident, it is strongly preferred to employ mixtures containing at least 50 mole percent of compounds in which R is hydrogen. If between 50 and 100 mole percent of such compounds are present in the mixture, the product will contain both the corresponding p-methylphenol and any other p-alkylphenols which correspond to the p-hydroxyalkylphenols utilized. In general, the mixture will also contain a corresponding phenol which is unsubstituted in the para position, the product of the formaldehyde-generating step.

The invention is illustrated by an example in which a quartz tube was charged with 20 cc. of quartz chips, 40 cc. of zinc oxide pellets and an additional 40 cc. of quartz chips. The tube was heated in air for two hours at a catalyst temperature of 480° C., after which a mixture of tetrahydrofuran and p-hydroxybenzyl alcohol in a 4:1 molar ratio was passed over the catalyst at a rate of 0.2 ml. per minute, together with an equal volume of water and air at the flow rate of 0.4 SCFH (standard cubic feet per hour). The effluent gas was chilled in a mixture of isopropyl alcohol and solid carbon dioxide; it was shown by gas chromatographic and spectral analysis to comprise 57% (by weight) phenol and 43% p-cresol.

What is claimed is:

1. A method for preparing a p-alkylphenol in which the para-substituent has the formula $CH_2R$, wherein R is hydrogen, an alkyl radical containing about 1-4 carbon atoms or phenyl, which comprises contacting at least one p-hydroxyalkylphenol in which the para-substituent has the formula

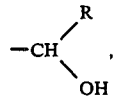

at least part of said p-hydroxyalkylphenol being one in which R is hydrogen, with water and oxygen at a temperature in the range of about 350°–550° C., in the presence of at least one oxide of a Group II metal having an atomic weight less than 70.

2. A method according to claim 1 wherein R is hydrogen.

3. A method according to claim 2 wherein the oxygen is provided by air.

4. A method according to claim 3 wherein the Group II metal is at least one of magnesium, calcium and zinc.

5. A method according to claim 4 wherein the reaction is effected at atmospheric pressure and a temperature within the range of about 450°–500° C.

6. A method according to claim 5 wherein the sole p-hydroxyalkylphenol used is p-hydroxybenzyl alcohol and the product is p-cresol.

7. A method according to claim 6 wherein the Group II metal is zinc.

* * * * *